(12) United States Patent
Tanaka et al.

(10) Patent No.: US 7,377,962 B2
(45) Date of Patent: May 27, 2008

(54) ELECTRIC DISCHARGE DEVICE AND AIR PURIFYING DEVICE

(75) Inventors: Toshio Tanaka, Sakai (JP); Kanji Motegi, Sakai (JP); Kenkichi Kagawa, Sakai (JP)

(73) Assignee: Daikin Industries, Ltd., Osaka (JP)

( * ) Notice: Subject to any disclaimer, the term of this patent is extended or adjusted under 35 U.S.C. 154(b) by 197 days.

(21) Appl. No.: 10/569,427

(22) PCT Filed: Jun. 22, 2004

(86) PCT No.: PCT/JP2004/009093

§ 371 (c)(1),
(2), (4) Date: Feb. 23, 2006

(87) PCT Pub. No.: WO2005/025021

PCT Pub. Date: Mar. 17, 2005

(65) Prior Publication Data

US 2006/0272505 A1    Dec. 7, 2006

(30) Foreign Application Priority Data

Aug. 29, 2003   (JP) .............................. 2003-307194

(51) Int. Cl.
*B03C 3/40* (2006.01)

(52) U.S. Cl. ....................... 96/83; 96/88; 96/95; 96/96; 96/98; 313/311; 313/357

(58) Field of Classification Search ............ 96/95–100, 96/65, 66, 83, 84, 69, 88; 95/58; 422/186.04; 313/292, 311, 357; 361/225–235
See application file for complete search history.

(56) References Cited

U.S. PATENT DOCUMENTS

| 4,666,474 | A | * | 5/1987 | Cook ............................. 96/90 |
| 4,822,381 | A | * | 4/1989 | Mosley et al. ................. 95/79 |
| 5,037,456 | A | * | 8/1991 | Yu ................................ 96/76 |
| 5,290,343 | A | * | 3/1994 | Morita et al. .................. 96/39 |
| 5,322,550 | A | * | 6/1994 | Park ............................. 96/66 |
| 5,433,772 | A | * | 7/1995 | Sikora .......................... 96/87 |
| 6,092,387 | A | * | 7/2000 | Hironaka et al. ............. 62/317 |
| 6,163,098 | A | * | 12/2000 | Taylor et al. ............... 310/308 |
| 6,524,369 | B1 | * | 2/2003 | Krigmont ..................... 95/78 |
| 6,579,349 | B1 | * | 6/2003 | Ting et al. .................... 96/44 |
| 6,679,940 | B1 | * | 1/2004 | Oda ............................. 96/55 |
| 2004/0065202 | A1 | * | 4/2004 | Gatchell et al. .............. 96/66 |

FOREIGN PATENT DOCUMENTS

| JP | 63-311365 | 12/1988 |
| JP | 4-293563 A | * 10/1992 |

(Continued)

*Primary Examiner*—Richard L Chiesa
(74) *Attorney, Agent, or Firm*—Global IP Counselors

(57) ABSTRACT

A discharge device for generating a streamer discharge includes a discharge electrode and a counter electrode. The discharge electrode is in a shape of a wire or rod and is disposed substantially parallel to the counter electrode. Thus, even when a tip of the discharge electrode becomes worn out, a shape of the tip of the discharge electrode remains unchanged and a distance between the discharge electrode and the counter electrode remains unchanged. As a result, even when the tip of the discharge electrode becomes worn out, the streamer discharge stability will not fall.

13 Claims, 9 Drawing Sheets

FOREIGN PATENT DOCUMENTS

| | | |
|---|---|---|
| JP | 11-067423 | 3/1999 |
| JP | 11-333244 | 12/1999 |
| JP | 2002-143634 | 5/2002 |
| JP | 2002-361028 | 12/2002 |
| JP | 2003-053129 | 2/2003 |
| WO | WO 01/19419 A1 * | 3/2001 |

* cited by examiner (A)

(B)

|  |  | A (mm) | | | | | |
|---|---|---|---|---|---|---|---|
|  |  | 3.8 | 4.0 | 4.2 | 4.4 | 4.6 | 5.0 |
| B (mm) | 4.2 | ○ | ◎ | × | ○ | ○ | × |
|  | 4.4 | ○ | △ | ○ | ○ | ○ | × |
|  | 4.6 | ○ | ◎ | ○ | △ | ○ | × |
|  | 4.8 | △ | ○ | ○ | ○ | ◎ | △ |
|  | 5.0 | △ | ○ | ◎ | ○ | ◎ | ○ |
|  | 5.2 | × | ◎ | ○ | ○ | ○ | ○ |
|  | 5.4 | × | ◎ | ○ | ○ | ○ | ○ |

| | | A (mm) | | | | | | | | | | |
|---|---|---|---|---|---|---|---|---|---|---|---|---|
| | | 3.8 | 4.0 | 4.2 | 4.4 | 4.6 | 4.8 | 5.0 | 5.2 | 5.4 | 5.6 | 5.8 |
| B(mm) | 4.4 | | | | | | | | | | | |
| | 4.6 | | | | | | | | | | | |
| | 4.8 | | | ◎ | ◎ | ◎ | ◎ | ○ | | | | |
| | 5.0 | | | ◎ | ◎ | ◎ | ◎ | ○ | | | | |
| | 5.2 | | | ◎ | ◎ | ◎ | ◎ | ○ | | | | |
| | 5.4 | | | ◎ | ◎ | ◎ | ◎ | ○ | | | | |
| | 5.6 | | | ◎ | ◎ | ◎ | ◎ | ○ | | | | |
| | 5.8 | | | ◎ | ◎ | ◎ | ◎ | ○ | | | | |
| | 6.0 | | | ◎ | ◎ | ◎ | ◎ | ○ | | | | |
| | 6.2 | | | ◎ | ◎ | ◎ | ◎ | ○ | | | | |
| | 6.4 | | | ◎ | ◎ | ◎ | ◎ | ○ | | | | |
| | 6.6 | | | ◎ | ◎ | ◎ | ◎ | ○ | | | | |

ELECTRIC DISCHARGE DEVICE AND AIR PURIFYING DEVICE

CROSS-REFERENCE TO RELATED APPLICATIONS

This U.S. National stage application claims priority under 35 U.S.C. §119(a) to Japanese Patent Application No. 2003-307194, filed in Japan on Aug. 29, 2003 the entire contents of which are hereby incorporated herein by reference.

TECHNICAL FIELD

This invention relates to a discharge device which generates a streamer discharge from the tip of a discharge electrode towards a counter electrode. The invention further relates to an air purifying device which employs such a type of discharge device.

BACKGROUND ART

Discharge devices for generating streamer discharges are known in the conventional art. One such discharge device is made up of a needle-like discharge electrode having a pointed tip and a sheet-like counter electrode (see for example JP, 2002-361028, A). In the discharge device of this patent gazette, the discharge electrode is positioned so as to be oriented perpendicularly to the surface of the counter electrode, with its tip positioned to lie adjacent to the counter electrode. The discharge device is configured, such that it generates a streamer discharge from the tip of the discharge electrode towards the counter electrode by application of discharge voltages to both the electrodes.

In the above-described discharge device, a low-temperature plasma is generated by streamer discharge. The low-temperature plasma contains substances of high reactivity (i.e., activated species such as electron, ion, ozone, and radical). And, such a type of discharge device is employed for example in air purifying devices which use a high-reactivity substance contained in a low-temperature plasma for decomposing and removing harmful substances and odorous substances in the air.

Problems that the Invention Intends to Solve

In a conventional discharge device, however, the tip of a discharge electrode wears by small degrees because of the effect of high-speed electrons and activated species which are generated during the discharge. As a result, the tip of the discharge electrode changes shape with time. And, when the tip of the pointed, needle-shaped discharge electrode becomes worn out, the diameter of the tip becomes somewhat increased. As a result, the distance between the discharge electrode and the counter electrode widens. Consequently, the discharge characteristic changes, and the streamer discharge becomes unstable. In addition, if voltages of higher level are applied with a view to coping with the increase in the distance between the discharge electrode and the counter electrode, this tends to arise problems such as spark generation.

With these problems in mind, the present invention was made. Accordingly, an object of the present invention is to prevent, in a discharge device which generates a streamer discharge from the tip of a discharge electrode towards a counter electrode, the streamer discharge stability from deteriorating even when the tip of the discharge electrode (41) becomes worn out.

SUMMARY OF THE INVENTION

The present invention is characterized in that a discharge electrode (41) in the shape of a wire or rod is disposed substantially parallel to a counter electrode (42) whereby, even when the tip of the discharge electrode (41) becomes worn out, the distance between the tip of the discharge electrode (41) and the counter electrode (42) remains unchanged.

More specifically, a first aspect of the present invention is directed to a discharge device which comprises a discharge electrode (41), a counter electrode (42) facing towards the discharge electrode (41), and power source means (45) for applying discharge voltages to both the electrodes (41, 42) and which is configured so as to generate a streamer discharge from the tip of the discharge electrode (41) towards the counter electrode (42). And, the discharge device of the first aspect of the present invention is characterized in that the discharge electrode (41) in the shape of a wire or rod is disposed substantially parallel to the counter electrode (42). In addition, a second aspect of the present invention provides a discharge device which is characterized in that the discharge electrode (41) in the shape of a wire or rod is disposed substantially parallel to the counter electrode (42) in the shape of a sheet. Here, the term "wire-shaped" or "rod-shaped" used to represent the shape of the discharge electrode (41) means any elongated shape whose cross sectional area is substantially constant. In addition, the "sheet-shaped" counter electrode (42) may have a flat surface shape or curved surface shape.

In the first and second aspect of the present inventions, a streamer discharge is generated from the tip of the discharge electrode (41) disposed substantially parallel to the counter electrode (42) towards the counter electrode (42). In this case, even when the tip of the discharge electrode (41) becomes worn out because of the effect of high-speed electrons and activated species which are generated during the discharge, the distance between the discharge electrode (41) and the counter electrode (42) is held constant because of the arrangement that the discharge electrode (41) is disposed substantially parallel to the counter electrode (42). In addition, the discharge electrode (41) is shaped like a wire or rod, and even when the discharge electrode (41) becomes worn out its tip shape remains unchanged. Accordingly, even when the discharge electrode (41) becomes worn out, the discharge characteristic is maintained, and streamer discharges are stably generated.

A third aspect of the present invention provides a discharge device according to the discharge device of the first aspect of the present invention which is characterized in that an electrode-faced member (43) is disposed in a position so as to face the counter electrode (42) across the discharge electrode (41), wherein the electrode-faced member (43) has an electrode-faced surface (43a) opposite to the counter electrode (42).

In the third aspect, by virtue of the arrangement that the electrode-faced member (43) having the electrode-faced surface (43a) is disposed such that the electrode-faced member (43) and the counter electrode (42) face each other across the discharge electrode (41), the streamer discharge becomes stabilized. More specifically, if the electric field convergence on the tip of the discharge electrode (41) becomes excessive, this results in causing, instead of a streamer discharge, a weak discharge such as a glow discharge to be generated. On the other hand, if the electrode-faced member (43) is provided whose electric potential is so set as to equal the electric potential of the discharge electrode (41) or to be near the electric potential of the discharge electrode (41), this makes it possible to relieve the electric field convergence on the tip of the discharge electrode (41) by the action of the electrode-faced surface (43a) of the electrode-faced member (43). Consequently, streamer discharges are stably generated.

A fourth aspect of the present invention provides a discharge device according to the discharge device of the third aspect of the present invention which is characterized in that the electrode-faced surface (43a) lies substantially parallel to both the discharge electrode (41) and the counter electrode (42).

In the fourth aspect of the present invention, even when the tip of the discharge electrode (41) gradually wears, not only the distance between the discharge electrode (41) and the counter electrode (42) but also the distance between the discharge electrode (41) and the electrode-faced surface (43a) remains unchanged. Consequently, the action of relieving the electric field convergence on the tip of the discharge electrode (41) becomes stable, whereby the streamer discharge becomes further stabilized.

A fifth aspect of the present invention provides a discharge device according to the discharge device of the fourth aspect of the present invention which is characterized in that the discharge electrode (41) is disposed either at a position intermediately between the counter electrode (42) and the electrode-faced surface (43a) or at a position nearer to the electrode-faced surface (43a) relative to the intermediate position. The "intermediate position" is a position where the distance between the counter electrode (42) and the electrode-faced surface (43a) is divided into two nearly equal parts.

Here, if the discharge electrode (41) is disposed nearer to the counter electrode (42) relative to the intermediate position, this impedes the action of the electrode-faced surface (43a) relieving the electric field convergence on the tip of the discharge electrode (41). As a result, instead of a streamer discharge, a glow discharge is likely to be generated. In the fifth aspect of the present invention, however, it is arranged such that the discharge electrode (41) is disposed either at the intermediate position or at the position nearer to the electrode-faced surface (43a) relative to the intermediate position. As a result of such arrangement, the action of relieving the electric field convergence on the tip of the discharge electrode (41) becomes stable. Consequently, streamer discharges are stably generated.

A sixth aspect of the present invention provides a discharge device according to the discharge device of the third aspect of the present invention which is characterized in that the electrode-faced member (43) and the discharge electrode (41) are formed of different materials.

In the sixth aspect of the present invention, for example, if the electrode-faced member (43) is brought into electric conduction with the discharge electrode (41), this allows the electric potential of the electrode-faced member (43) to equal the electric potential of the discharge electrode (41) or to be near the electric potential of the discharge electrode (41). This accordingly creates an action of relieving the electric field convergence on the discharge electrode (41), thereby making it possible to stabilize the streamer discharge, almost in the same way as the above.

A seventh aspect of the present invention provides a discharge device according to the discharge device of the sixth aspect of the present invention which is characterized in that the electrode-faced member (43) is formed of an insulating material.

In the seventh aspect of the present invention, during the discharge, electric charges are accumulated in the electrode-faced member (43) (formed of an insulating material) by induced polarization on the electrode-faced member (43), and the electric potential of the electrode-faced member (43) gradually approaches that of the discharge electrode (41). After all, the electrode-faced member (43) acts to relieve the electric field convergence on the tip of the discharge electrode (41). Accordingly, streamer discharges are stably generated, almost in the same way as the above.

An eighth aspect of the present invention provides a discharge device according to the discharge device of the third aspect of the present invention which is characterized in that a fixing member (44) for firmly fixing the discharge electrode (41) to the electrode-faced member (43) is provided, and that the tip of the discharge electrode (41) projects from the fixing member (44).

In the eighth aspect of the present invention, streamer discharges are generated from the tip of the discharge electrode (41) projecting from the fixing member (44) towards the counter electrode (42). And, in the eighth aspect of the present invention, since the discharge electrode (41) is firmly fixed to the electrode-faced member (43) with the fixing member (44), the position of the discharge electrode (41) relative to the counter electrode (42) and to the electrode-faced member (43) becomes stable. As a result, the streamer discharge becomes stable.

A ninth aspect of the present invention provides a discharge device according to the discharge device of the third aspect of the present invention which is characterized in that a relational expression (1) represented as: $0.96 \leq B/A \leq 1.52$ is satisfied where A is the spacing dimension between the discharge 25 electrode (41) and the electrode-faced surface (43a) and B is the spacing dimension between the discharge electrode (41) and the counter electrode (42).

Here, the condition, in which a streamer discharge changes state to a glow discharge or to a spark when the spacing dimension, A, between the discharge electrode (41) and the electrode-faced surface (43a) and the spacing dimension, B, between the discharge electrode (41) and the counter electrode (42) are varied, is described. FIG. 9 graphically shows a discharge tendency in which the horizontal axis represents the spacing dimension, A, between the discharge electrode (41) and the electrode-faced surface (43a) while the vertical axis represents the spacing dimension, B, between the discharge electrode (41) and the counter electrode (42). In the figure, if the value of the spacing dimension, A, increases or the value of the spacing dimension, B, decreases with respect to the hatched streamer discharge region, there is a change to the glow discharge region. On the other hand, if the value of the spacing dimension, A, decreases or the value of the spacing dimension, B, increases with respect to the hatched streamer discharge region, there is a change to the spark region. In other words, if the value of B/A is an intermediate value, this means the streamer discharge region. As the value of B/A decreases it becomes more likely that there is a change to the glow discharge region. On the other hand, as the value of B/A increases it becomes more likely that there is a change to the spark region.

On the other hand, there are electrode manufacturing errors. Therefore, when considering a specific manufacturing error, both a spark and a glow discharge are generated in the states (a) and (b) of FIG. 9. Accordingly, even when there is a manufacturing error, the size of electrodes must fall within the range so that the state (c) where streamer discharges are generated without fail is obtained. The value of this error is preferably about ±0.3 mm relative to the design value (the error range is about 0.6 mm). If the error value is less than that, this makes it difficult to fabricate electrodes. On the other hand, if the error value is greater than that, this produces the requirement for the increase in discharge voltage level.

Next, for the values of the spacing dimension, A, and the spacing dimension, B, there are combinations in which the streamer discharge becomes stable and, on the other hand, there are combinations in which the streamer discharge becomes unstable. These combinations are shown in tables of FIGS. 10 and 14. Referring first to a table of FIG. 10, for a discharge electrode having a diameter dimension of Φ0.14 mm, the value of the spacing dimension, A, is varied from 3.8 mm up to 5.0 mm at intervals of 0.2 mm while on the other hand the value of the spacing dimension, B, is varied from 4.2 mm up to 5.4 mm at intervals of 0.2 mm, and the discharge stability is represented by symbols for every combination. The symbols used here are indexes indicative of the rate at which a streamer discharge is stably generated. More specifically, combinations in which no streamer discharge is generated are marked by a symbol of X, and combinations in which a streamer discharge is generated even when the applied voltage is varied are marked by symbols of Δ, ◯, and ⊚. Especially, the symbol Δ indicates combinations in which a streamer discharge is generated only when the variation range of the applied voltage is narrow (the variation range is smaller than 0.4 kV). The symbol ◯ indicates combinations in which the variation range is intermediate (the variation range is not less than 0.4 kV nor more than 0.9 kV). The symbol ⊚ indicates combinations in which a streamer discharge is generated even when the variation range is great (the variation rang is greater than 1.0 kV).

In the table, if the value of the spacing dimension, A, is in the range between 4.0 mm and 4.6 mm, and if the value of the spacing dimension, B, is in the range between 4.8 mm and 5.4 mm, then the error of the value of the spacing dimension, A, and the error of the value of the spacing dimension, B, each fall within ±0.3 mm and, in addition, in every combination the stability of the discharge streamer is marked by ◯ or ⊚. Accordingly, for the case of a discharge electrode having a diameter dimension of Φ0.14 0mm, it becomes possible to generate stable streamer discharges if the B/A value falls within the range of the value of these combinations, in other words 1.04≦B/A≦1.35.

Referring now to a table of FIG. 14, for a discharge electrode having a diameter dimension of Φ0.2 mm, the value of the spacing dimension, A, is varied from 4.2 mm up to 5.0 mm at intervals of 0.2 mm while on the other hand the value of the spacing dimension, B, is varied from 4.8 mm up to 6.4 mm at intervals of 0.2 mm, and the discharge stability is represented by symbols for every combination. As shown in the table, in every combination the discharge results of the streamer discharge are marked by ◯ or ⊚. Accordingly, any combination within this range may be selected, and the B/A value becomes 0.96≦B/A≦1.52. It suffices if the value of the spacing dimension, A, and the value of the spacing dimension, B, are selected from within the range in which the error of each value falls within ±0.3 mm. For example, if a range, in which the value of the spacing dimension, A, is in the range between 4.4 mm and 5.0 mm and the value of the spacing dimension, B, is in the range between 5.8 mm and 6.4 mm, is selected, then the B/A value becomes 1.16≦B/A≦1.45.

The above proves that although the optimum range of the B/A value somewhat differs depending on the diameter dimension of the discharge electrode it exhibits almost the same tendency, and that if it is arranged such that the error of each of the value of the spacing dimension, A, and the value of the spacing dimension, B, falls within ±0.3 mm within the range of 0.96≦B/A≦1.52 this facilitates manufacture and provides generally good results.

A tenth aspect of the present invention provides a discharge device according to the discharge device of the third aspect of the present which is characterized in that the electrode-faced member (43) is formed by a member having a predetermined width dimension, D, in the direction perpendicular to the axis of the discharge electrode (41), and that a relational expression (2) represented as: A≦D is satisfied where A is the spacing dimension between the discharge electrode (41) and the electrode-faced surface (43a) and D is the width dimension of the electrode-faced member (43).

Here, conversely to the relational expression (2), if the spacing dimension, A, exceeds the width dimension, D, the action of relieving the electric field convergence on the tip of the discharge electrode (41) deteriorates. As a result, it becomes more likely that a glow discharge is generated. In the tenth aspect of the present invention, however, the discharge is less prone to becoming a glow discharge, thereby making it possible to stably generate a streamer discharge.

An eleventh aspect of the present invention provides a discharge device according to the discharge device of the third aspect of the present invention which is characterized in that a relational expression (3) represented as: B/E≧20 is satisfied where E is the width dimension of the discharge electrode (41) relative to the surface direction of the counter electrode (42) or the diameter dimension of the discharge electrode (41) and B is the spacing dimension between the discharge electrode (41) and the counter electrode (42).

Here, conversely to the relational expression (3), if the B/E value falls below 20, the width or the diameter of the discharge electrode (41) becomes great relative to the distance between the discharge electrode (41) and the counter electrode (42). As a result, the discharge characteristic tends to change due to the worn-out shape of the tip of the discharge electrode (41) and its variation; the streamer discharge becomes unstable; and when the discharge electrode (41) is provided in a plural number the discharge becomes uneven at each discharge electrode. However, if it is arranged such that B/E≧20 holds, this makes the width or the diameter of the discharge electrode (41) small enough relative to the distance between the discharge electrode (41) and the counter electrode (42). This reduces the effect that the worn-out shape of the tip of the discharge electrode (41) and its variation have on the discharge, thereby making it possible to generate stable streamer discharges. In addition, if it is arranged such that B/E>30 holds, the discharge sound of streamer discharges is turned down.

A twelfth aspect of the present invention provides a discharge device according to the discharge device of the first aspect of the present invention which is characterized in that the power source means (45) is formed by a direct-current power source.

In the twelfth aspect of the present invention, a high direct-current voltage is applied to the discharge electrode (41), thereby to create a predetermined potential difference between the discharge electrode (41) and the counter electrode (42). As a result, a streamer discharge is generated from the tip of the discharge electrode (41) towards the counter electrode (42).

A thirteenth aspect of the present invention provides a discharge device according to the discharge device of the first aspect of the present invention which is characterized in that the discharge electrode (41) is formed of a tungsten material.

In the case where, as in the thirteenth aspect of the present invention, tungsten material is used for electrode formation, the discharge electrode (41) undergoes less warpage and deformation because the tungsten material has a high degree of hardness, thereby facilitating the manufacture of electrodes. In addition, since the tungsten material has a high melting point and a high degree of heat conductivity, this reduces the wear of the discharge electrode (41) due to the discharge, thereby enhancing the durability thereof. In addition, the tungsten material has characteristics that, when the tip of the discharge electrode (41) becomes worn out by small degrees with the discharge, the tip of the discharge electrode (41) becomes rough. This contributes to accomplishing improvement in streamer discharge stability.

A fourteenth aspect of the present invention is directed to an air purifying device (10) which comprises an air passageway (25) through which air to be treated flows, and a discharge device (40), disposed in the air passageway (25), for generating a streamer discharge. And, the air purifying device (10) is characterized in that the discharge device (40) of the fourteenth aspect of the present invention is formed by the discharge device (40) as set forth in the first aspect of the present invention.

In the fourteenth aspect of the present invention, by making utilization of high-reactivity substances (i.e., activated species such as electron, ion, ozone, and radical) contained in a plasma generated by streamer discharges in the discharge device (40), harmful substances and odorous substances in air to be treated are decomposed and removed. In addition, a catalyst may be used if needed, and in the presence of the catalyst the aforesaid high-reactivity substances are brought into reaction with harmful substances and odorous substances for decomposing and removing these substances.

Effects

In accordance with the first and second aspect of the present inventions, the wire- or rod-shaped discharge electrode (41) is disposed substantially parallel to the sheet-shaped counter electrode (42) so that even when the tip of the discharge electrode (41) becomes worn out the distance between the discharge electrode (41) and the counter electrode (42) is held constant and the shape of the tip of the discharge electrode (41) remains unchanged. Therefore, the discharge characteristic is maintained and it becomes possible to stabilize the streamer discharge. Accordingly, problems, such as spark generation due to the change in shape of the discharge electrode (41) with time, can be avoided.

In accordance with the third aspect of the present invention, it is arranged such that the electrode-faced member (43) having the electrode-faced surface (43a) is disposed in a position so as to face the counter electrode (42) with the discharge electrode (41) interposed therebetween. As a result of such arrangement, it becomes possible to relieve the electric field convergence on the tip of the discharge electrode (41), thereby making it possible to further stabilize the streamer discharge.

In accordance with the fourth aspect of the present invention, it is arranged such that the electrode-faced surface (43a) lies substantially parallel to both the discharge electrode (41) and the counter electrode (42). As a result of such arrangement, even when the tip of the discharge electrode (41) becomes worn out with time, not only the distance between the discharge electrode (41) and the counter electrode (42) but also the distance between the discharge electrode (41) and the electrode-faced surface (43a) remains unchanged, thereby making it possible to still further stabilize the streamer discharge.

In accordance with the fifth aspect of the present invention, it is arranged such that the discharge electrode (41) is disposed either at a position intermediately between the counter electrode (42) and the electrode-faced surface (43a) or at a position nearer to the electrode-faced surface (43a) relative to the intermediate position. Such arrangement assures that the action of relieving the electric field convergence on the tip of the discharge electrode (41) is created, and streamer discharges are stably generated.

In accordance with the sixth aspect of the present invention, it is arranged such that the electrode-faced member (43) formed of a different material from the discharge electrode (41) is employed and the electric potential of the electrode-faced member (43) is set such that the electric field convergence in the discharge electrode (41) is relieved. As a result of such arrangement, the streamer discharge is stabilized.

In accordance with the seventh aspect of the present invention, during the discharge, electric charges are accumulated in the electrode-faced member (43) formed of insulating material, and the electric potential of the electrode-faced member (43) gradually approaches the electric potential of the discharge electrode (41). Consequently, the electrode-faced surface (43a) of the electrode-faced member (43) acts, in the same way as above, so as to relieve the electric field convergence in the discharge electrode (41), whereby streamer discharges are stably generated.

In accordance with the eighth aspect of the present invention, it is arranged such that the fixing member (44) for firmly fixing the discharge electrode (41) to the electrode-faced member (43) is provided and the tip of the discharge electrode (41) projects from the fixing member (44). As a result of such arrangement, the positional relationship between the discharge electrode (41), and the counter electrode (42) and the electrode-faced member (43) becomes stable, and the streamer discharge is stabilized accordingly.

In accordance with the ninth aspect of the present invention, it is arranged such that the spacing dimension, A, between the discharge electrode (41) and the electrode-faced surface (43a) and the spacing dimension, B, between the discharge electrode (41) and the counter electrode (42) are set so that the relational expression (1) represented as: $0.96 \leq B/A \leq 1.52$ is satisfied. Such arrangement is less prone to generating glow discharges or sparks, and it becomes possible to generate stable streamer discharges.

In accordance with the tenth aspect of the present invention, it is arranged such that the electrode-faced member (43) is formed by a member having a predetermined width dimension, D, in the direction perpendicular to the axis of the discharge electrode (41), and that a relational expression (2) represented as: $A \leq D$ is satisfied where A is the spacing dimension between the discharge electrode (41) and the electrode-faced surface (43a) and D is the width dimension of the electrode-faced member (43). As a result of such arrangement, the discharge is less prone to becoming a glow discharge, and it becomes possible to generate stable streamer discharges.

In accordance with the eleventh aspect of the present invention, it is arranged such the width dimension of the discharge electrode (41) relative to the surface direction of the counter electrode (42) or the diameter dimension of the discharge electrode (41), E, and the spacing dimension, B, between the discharge electrode (41) and the counter electrode (42) are set such that the relational expression (3) represented as: B/E≧20 is satisfied. As a result of such arrangement, the width or diameter of the discharge electrode (41) is reduced sufficiently relative to the distance between the discharge electrode (41) and the counter electrode (42), thereby reducing the effect that the worn-out shape of the tip of the discharge electrode (41) and its variation have on the discharge. Accordingly, it becomes possible to generate stable streamer discharges. Especially, if B/E≧30, this makes it possible to turn down the discharge sound of streamer discharges.

In accordance with the twelfth aspect of the present invention, it is arranged such that the power source means (45) is formed by a direct-current power source. As a result of such arrangement, it becomes possible to manufacture discharge devices at lower costs in comparison with the case where pulse power sources are employed.

In accordance with the thirteenth aspect of the present invention, it is arranged such that the discharge electrode (41) is made of tungsten. Such arrangement provides the following advantages. The manufacture of the discharge electrode (41) is facilitated. Besides, the durability of the discharge electrode (41) is improved and streamer discharges are stably generated.

Finally, in accordance with the fourteenth aspect of the present invention, the stability of the streamer discharge is enhanced in an air purifying device provided with a discharge device which generates a streamer discharge and, consequently, it becomes possible to stabilize the capability to purify air.

BRIEF DESCRIPTION OF THE DRAWINGS

FIG. 3 is a diagram which illustrates the dimensional structure of the discharge device, wherein FIG. 3(A) is a side view and FIG. 3(B) is a front view;

FIG. 13 is comprised of FIGS. 13(A) and 13(B), wherein FIG. 13(A) is a diagram which illustrates in enlarged manner a major section of the electrode structure of the discharge device and FIG. 13(B) is a horizontal cross sectional view of the discharge device; and FIG. 14 is a table which represents the electrode dimensional structure and the streamer discharge stability.

DETAILED DESCRIPTION OF THE INVENTION

Hereinafter, embodiments of the present invention are described in detail with reference to the drawings.

First Embodiment of the Invention

A first embodiment of the present invention is first described with reference to FIGS. 1-3.

Figure 1:
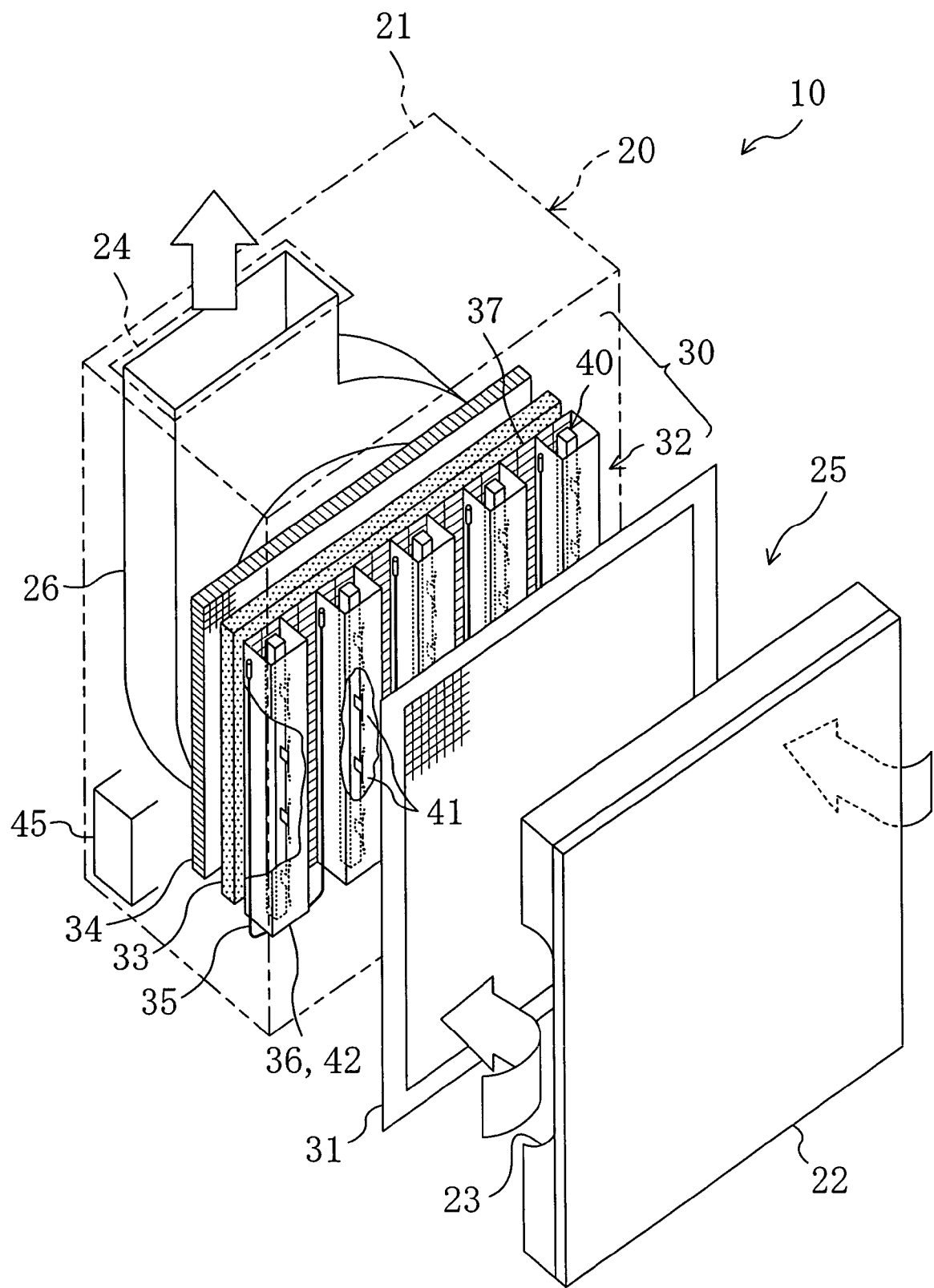
FIG. 1 is an exploded perspective view of an air purifying device according to a first embodiment of the present invention.
Figure 2:
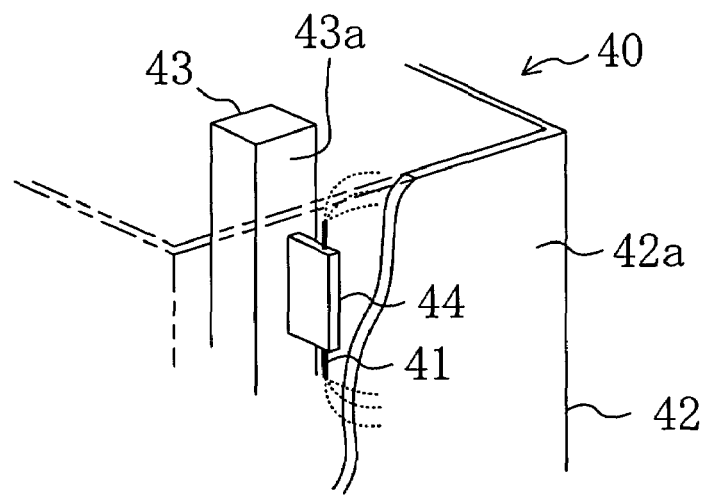
FIG. 2 is a perspective view which illustrates in enlarged manner a major section of a discharge device.

FIG. 1 is an exploded perspective view of an air purifying device (10) according to the first embodiment. The air purifying device (10) is a household air purifying device for general household/smaller store use.

The air purifying device (10) includes a casing (20). The casing (20) is made up of a box-like casing main body (21) one end of which is opened and a front plate (22) which is mounted to the open end. Formed in each side surface of the casing (20) on the side of the front plate (22) is an air suction opening (23). In addition, the casing main body (21) has an air blowout opening (24) which is formed in a portion of the top plate adjacent to the back plate.

Formed within the casing (20) is an air passageway (25) through which room air, i.e., an air stream to be treated, flows from the air suction opening (23) to the air blowout opening (24). Arranged, in sequence from the upstream side of the flow of air, along the air passageway (25) are a functional section (30) including various components for air cleaning, and a centrifugal air blower (26) for distribution of room air through the air passageway (25).

Disposed, in sequence from the side of the front plate (22), in the functional section (30) are a pre-filter (31), an ionization part (32), an electrostatic filter (33) as a dust collecting filter, and a catalytic filter (34). A discharge device (40) for causing a plasma of low temperature to be generated is integrally incorporated into the ionization part (32).

The pre-filter (31) is disposed to entrap and collect dust of relatively large size contained in the room air.

The ionization part (32) causes dust of relatively small size passing through the pre-filter (31) to be charged electrically. The electrically charged dust is entrapped and collected by the electrostatic filter (33) positioned downstream of the ionization part (32). The ionization part (32) is made up of a plurality of ionization lines (35) and a plurality of counter electrodes (36). These plural ionization lines (35) each extend across the ionization part (32) from the top end to the bottom end at even intervals. Each ionization line (35) lies on a single virtual surface in parallel with the electrostatic filter (33). The counter electrode (36) is an elongated member having a cross section in the shape of a Japanese katakana character "コ" and extending vertically. The counter electrode (36) is disposed between ionization lines (35), such that it is positioned parallel to the ionization lines (35). The counter electrode (36) is positioned such that its "コ"-shaped opening side faces towards the downstream side of the flow of air. And, each counter electrode (36) is joined, at a respective opening end, to a single mesh plate (37).

The discharge device (40) has a discharge electrode (41) and a counter electrode (42) which is a shared electrode serving also as the counter electrode (36) of the ionization part (32). The discharge electrode (41) is disposed within the counter electrode (42). More specifically, a vertically-extending electrode holding member (electrode-faced member) (43) is provided within the counter electrode (42), as shown in FIG. 2 which is a major-section enlarged perspective view of FIG. 1. The discharge electrode (41) is firmly fixed, through a fixing member (44), to the electrode holding member (43). The discharge electrode (41) is a wire- or rod-shaped electrode. The discharge electrode (41) is positioned such that its portion projecting from the fixing member (44) lies substantially parallel to a front portion (42a) of the counter electrode (42).

In the above-described configuration, the electrode holding member (43) is disposed in a position so as to face the front portion (42a) of the counter electrode (42) across the discharge electrode (41). In addition, the electrode holding member (43) and the fixing member (44) are formed of a metal material. The discharge electrode (41) and the electrode holding member (43) conduct with each other through the fixing member (44). The electrode holding member (43) has an electrode-faced surface (43a) which lies substantially parallel to both the discharge electrode (41) and the counter electrode (42). And, the discharge electrode (41) is disposed at a position nearer to the electrode-faced surface (43a) relative to the intermediate position between the front portion (42a) of the counter electrode (42) and the electrode-faced surface (43a) of the electrode holding member (43).

The discharge device (40) is provided with a high-voltage direct-current power source (power source means) (45) which applies discharge voltages to both the discharge electrode (41) and the counter electrode (42). The high-voltage power source (45) may serve as a power source for supplying power to the ionization part (32).

Figure 3:
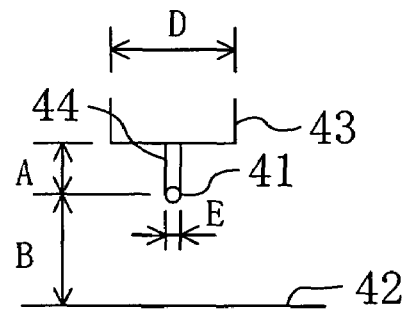
Figure 3:
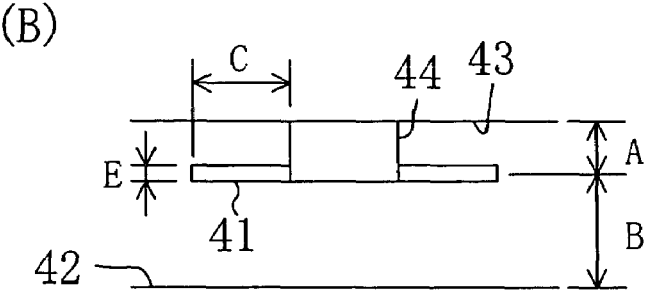

Here, the concrete configuration of each part of the discharge device (40) is described by making reference to FIG. 3. With reference first to FIG. 3, a relational expression (1) represented as: $0.96 \leq B/A \leq 1.52$ (more specifically, $1.04 \leq B/A \leq 1.35$) is satisfied where A is the spacing dimension between the discharge electrode (41) and the electrode-faced surface (43a) and B is the spacing dimension between the discharge electrode (41) and the counter electrode (42). The concrete numerical value of the spacing dimension, A, is as follows: $4.0 \leq A (mm) \leq 4.6$ ($4.3 \pm 0.3$) while on the other hand the concrete numerical value of the spacing dimension, B, is as follows: $4.8 \leq B (mm) \leq 5.4$ ($5.1 \pm 0.3$). In addition, a relational expression (2) represented as: $A \leq D$ is satisfied where A is the spacing dimension between the discharge electrode (41) and the electrode-faced surface (43a) and D is the width dimension of the electrode holding member (43) in the direction perpendicular to the axis of the discharge electrode (41). Furthermore, a relational expression (3) represented as: $B/E \geq 20$ is satisfied where E is the width dimension of the discharge electrode (41) relative to the surface direction of the counter electrode (42) or the diameter dimension of the discharge electrode (41) and B is the spacing dimension between the discharge electrode (41) and the counter electrode (42).

The discharge electrode (41) is formed of a wire of tungsten whose diameter dimension, E, is Φ0.14 mm and whose length dimension, C, i.e., the projection dimension of the discharge electrode (41) from the fixing member (44), is 8 mm. The tungsten wire is composed of a tungsten material with a purity of not less than 99%.

The catalytic filter (34) is disposed downstream of the electrostatic filter (33). The catalytic filter (34) is formed, for example, by a honeycomb-structure substrate which supports on its surface a catalyst. As the catalyst, catalysts (such as catalysts of the manganese family and catalysts of the precious metal family) capable of further activating high-reactivity substances in a low-temperature plasma generated by discharges and of promoting the decomposition of harmful substances and odorous substances in the air may be used.

Running Operation

Next, the running operation of the air purifying device (10) is described.

When the air purifying device (10) is in operation, the centrifugal air blower (26) starts operating and room air, i.e., a stream of air to be treated, flows and passes through the air passageway (25) within the casing (20). In addition, in this state, voltages are applied, by the DC power source (45), to the ionization part (32) and to the discharge device (40).

Upon introduction of the room air into the casing (20), dust of relatively large size is first removed by the pre-filter (31). During the passage of the room air through the ionization part (32), dust of relatively small size in the room air enters an electrically charged state, and the room air flows downstream, and the relatively small size dust is entrapped and collected by the electrostatic filter (33). In the way as described above, airborne dust particles of from relatively small size to relatively large size are almost removed.

In the discharge device (40) integrally incorporated into the ionization part (32), a low-temperature plasma is being generated by streamer discharge. Since an ion wind generated during the discharge is reflected from the counter electrode (42) and then flows downstream of the air passageway (25), the generated low-pressure plasma rides on the ion wind, passes through the mesh plate (37), and flows downstream together with the process air. The low-temperature plasma contains high-reactivity substances (activated species such as electron, ion, ozone, and radical). When these high-reactivity substances arrive at the catalytic filter (34), they are further activated, thereby decomposing and removing harmful substances and odorous substances in the air. And, the clean room air, free from dust and from harmful and odorous substances, is blown out into the room through the air blowout opening (24).

Here, streamer discharges are generated from the tip of the discharge electrode (41) towards the counter electrode (42), which means that the tip of the discharge electrode (41) becomes gradually worn out with time due to high-speed electrons and activated species generated during the discharge. In the present embodiment, however, it is arranged such that the discharge electrode (41) is disposed substantially parallel to the front portion (42a) of the counter electrode (42). As a result of such arrangement, even when the tip of the discharge electrode (41) becomes worn out, the distance between the discharge electrode (41) and the counter electrode (42) is held constant. Besides, the discharge electrode (41) is in the shape of a wire or in the shape of a rod, so that, even when worn out, its tip shape remains unchanged. Accordingly, the discharge characteristic is maintained, even when the discharge electrode (41) becomes worn out, whereby streamer discharges are stably generated.

In addition, the electrode holding member (43) having the electrode-faced surface (43a) is disposed in a position so as to face the counter electrode (42) across the discharge electrode (41), thereby enhancing the streamer discharge stability. More specifically, if the electric field convergence on the tip of the discharge electrode (41) becomes excessive, this is prone to causing, instead of a streamer discharge, a weak discharge such as a glow discharge to be generated. On the other hand, if the electrode-faced surface (43a) lies in a position at a specific distance apart from the discharge electrode (41) and if a high voltage at the same electric potential as the discharge electrode (41) is applied to the electrode holding member (43), it becomes possible to relieve the electric field convergence on the tip of the discharge electrode (41). As a result, the streamer discharge becomes stable. The electrode holding member (43) is not necessary identical in electric potential with the discharge electrode (41). That is, any electric potential suffices if the electric field convergence on the tip of the discharge electrode (41) is relieved.

Furthermore, owing to the arrangement that the electrode-faced surface (43a) is disposed substantially parallel to the discharge electrode (41) and to the counter electrode (42), neither the distance between the discharge electrode (41) and the counter electrode (42) nor the distance between the discharge electrode (41) and the electrode-faced surface (43a) changes, even when the tip of the discharge electrode (41) becomes worn out with time. Accordingly, the streamer discharge stability is further enhanced.

In addition, if the discharge electrode (41) is disposed nearer to the counter electrode (42) relative to the electrode-faced surface (43a), this is prone to causing, instead of a streamer discharge, a weak discharge (such as a glow discharge) to be generated. The discharge electrode (41) is, however, disposed nearer to the electrode-faced surface (43a) relative to the counter electrode (42). As a result, streamer discharges are stably generated.

Furthermore, since the discharge electrode (41) is firmly fixed to the electrode holding member (43) with the fixing member (44), this stabilizes the positional relationship between the discharge electrode (41), and the counter electrode (42) and the electrode holding member (43). Also by this, the streamer discharge becomes stable.

Next, the operation by the concrete configuration of each part in FIG. 3 is described.

As described above, the discharge device of the present embodiment satisfies the foregoing three relational expressions, namely the relational expression (1) represented as: $0.96 \leq B/A \leq 1.52$ (more specifically, $1.04 \leq B/A \leq 1.35$) where A is the spacing dimension between the discharge electrode (41) and the electrode-faced surface (43a) and B is the spacing dimension between the discharge electrode (41) and the counter electrode (42); the relational expression (2) represented as: $A \leq D$ where A is the spacing dimension between the discharge electrode (41) and the electrode-faced surface (43a) and D is the width dimension of the electrode holding member (43) in the direction perpendicular to the axis of the discharge electrode (41); and the relational expression (3) represented as: $B/E \geq 20$ where E is the width dimension of the discharge electrode (41) relative to the surface direction of the counter electrode (42) or the diameter dimension of the discharge electrode (41) and B is the spacing dimension between the discharge electrode (41) and the counter electrode (42).

Figures 9, 10:
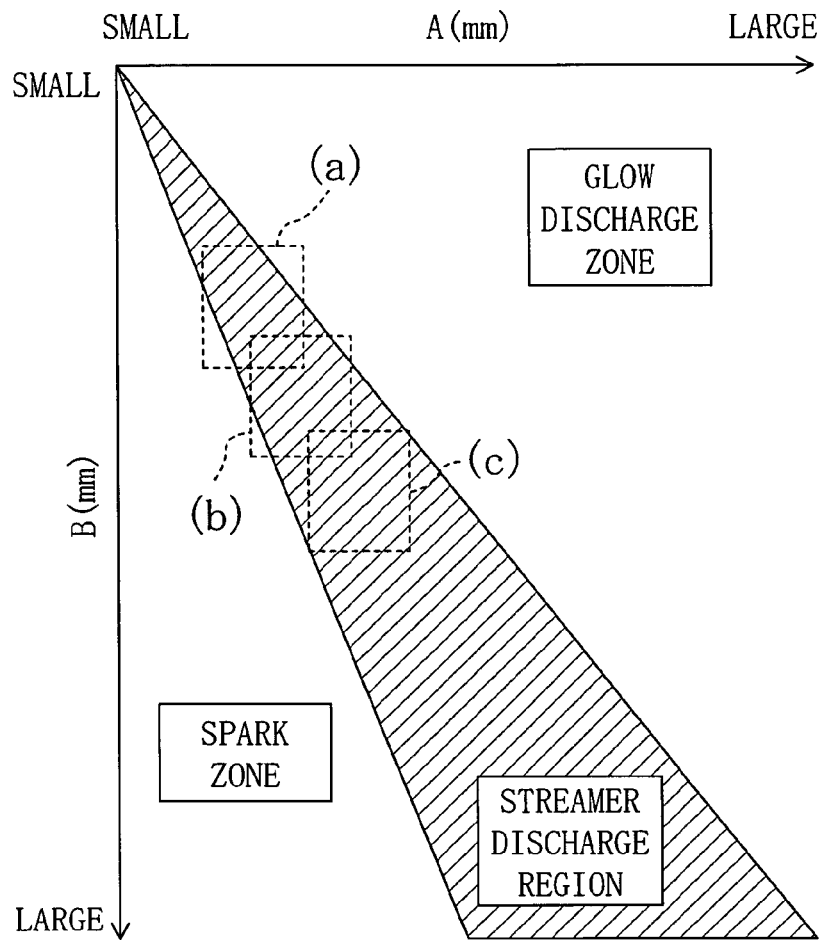
FIG. 9 is a graph which represents a relationship between the electrode dimensional structure and the discharge tendency.
FIG. 10 is a table which represents the electrode dimensional structure and the streamer discharge stability.

With regard to the relational expression (1), as already described by making use of FIGS. 9 and 10, if the value of B/A falls below 1.04, this becomes prone to causing a glow discharge to be generated. On the other hand, if the value of B/A exceeds 1.35, this increases the tendency towards spark generation. As a result, the maintenance of generating stable discharges becomes difficult. Further, simultaneous generation of discharges at a plurality of points becomes difficult. On the other hand, if $1.04 \leq B/A \leq 1.35$, this becomes less prone to causing a glow discharge or spark to be generated. As a result, it becomes possible to generate a stable streamer discharge.

With regard to the relational expression (2), if the spacing dimension, A, becomes greater than the width dimension, D, this weakens the action of the electrode-faced surface (43a) relieving the electric field convergence on the tip of the discharge electrode (41). On the other hand, if it is arranged such that the relational expression (2) represented as: $A \leq D$ is satisfied, this assures that the action of relieving the electric field convergence on the tip of the discharge electrode (41) is obtained, thereby making it possible to generate stable streamer discharges.

Additionally, with regard to the relational expression (3), if B/E is less than 20, this increases the width or the diameter of the discharge electrode (41) relative to the distance between the discharge electrode (41) and the counter electrode (42). As a result, the discharge characteristic becomes prone to change due to the wear of the tip of the discharge electrode (41) and its variation, and the streamer discharge becomes unstable and discharges in a plurality of discharge electrodes (41) become uneven. On the other hand, if $B/E \geq 20$, this makes the width or the diameter of the discharge electrode (41) small enough relative to the distance between the discharge electrode (41) and the counter electrode (42), thereby reducing the effect that the wear of the tip of the discharge electrode (41) and its variation have on the discharge. As a result, it becomes possible to provide stable streamer discharges. In addition, if it is arranged such that $B/E \geq 30$, this turns down the sound of streamer discharges.

Effects of the First Embodiment

As described above, in the first embodiment, the discharge electrode (41) in the shape of a wire or rod is disposed substantially parallel to the counter electrode (42) in the shape of a sheet so that, even when the tip of the discharge electrode (41) becomes worn out, the distance between the discharge electrode (41) and the counter electrode (42) is held constant and the shape of the tip of the discharge electrode (41) remains unchanged. Therefore, it becomes possible to maintain the discharge characteristic, and the streamer discharge is stabilized. Accordingly, problems, such as the generation of a spark due to the change in shape of the discharge electrode (41) with time and the generation of a glow discharge instead of the generation of a streamer discharge, can be avoided.

In addition, because of the arrangement that the electrode holding member (43) is disposed face to face with the counter electrode (42) with the discharge electrode (41) interposed therebetween, it becomes possible to relieve the electric field convergence on the tip of the discharge electrode (41), whereby the streamer discharge is further stabilized.

Furthermore, it becomes possible to generate stable streamer discharges by the following arrangements: the electrode-faced surface (43a) is disposed substantially parallel to the discharge electrode (41) and to the counter electrode (42) so that, even when the tip of the discharge electrode (41) becomes gradually worn out, neither the distance between the discharge electrode (41) and the counter electrode (42) nor the distance between the discharge electrode (41) and the electrode-faced surface (43a) changes; the discharge electrode (41) is disposed nearer to the electrode-faced surface (43a) relative to the counter electrode (42) so that a glow discharge is less prone to being generated; the fixing member (44) for firmly fixing the discharge electrode (41) to the electrode holding member (43) is provided so that the positional relationship between the discharge electrode (41), and the counter electrode (42) and the electrode holding member (43) is made stable; and the foregoing relational expressions (1)-(3) are satisfied.

In addition, in the present embodiment, the power source means (45) is formed by a direct-current power source, thereby making it possible to manufacture the discharge device (40) at lower costs in comparison with the case where pulse power sources are employed.

Furthermore, the discharge electrode (41) is formed of a material of tungsten.

Since the tungsten material has a high degree of hardness, the discharge electrode (41) undergoes less warpage or deformation, thereby facilitating the manufacture thereof. In addition, since the tungsten material has a high melting point and a high degree of heat conductivity, this reduces the wear of the discharge electrode (41) due to the discharge, thereby enhancing the durability thereof. In addition, the tungsten material has characteristics that, when the tip of the discharge electrode (41) becomes worn out by small degrees with the discharge, the tip becomes rough, thereby accomplishing improvement in streamer discharge stability.

Variational Example of the First Embodiment

In the first embodiment, the electrode holding member (43) and the fixing member (44) may be formed of the same kind of metal material as the discharge electrode (41). Alternatively, the electrode holding member (43) and the fixing member (44) may be formed of a different kind of metal material from the discharge electrode (41). In both cases, since the discharge electrode (41) and the electrode holding member (43) electrically conduct with each other through the fixing member (44), this makes it possible to relive the electric field convergence on the tip of the discharge electrode (41) during the discharge.

In addition, it may be arranged such that the electrode holding member (43) is formed of an insulating material while on the other hand the fixing member (44) is formed of a conducting material. In this case, electric charges are accumulated in the electrode 20 holding member (43) by induced polarization during the discharge, and the electric potential of the electrode holding member (43) gradually approaches the electric potential of the discharge electrode (41). Consequently, the electrode-faced surface (43*a*) of the electrode holding member (43) likewise acts so as to relieve the electric field convergence on the tip of the discharge electrode (41). Accordingly, also in this case, streamer discharges are stably generated.

Second Embodiment of the Invention

Figure 4:
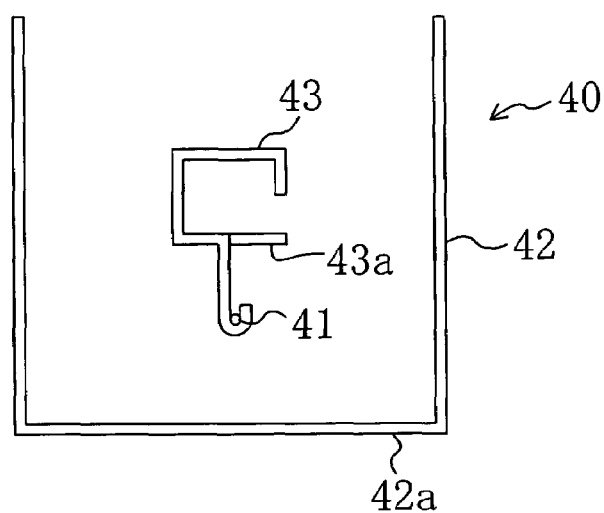
FIG. 4 is a constructional diagram of a discharge device according to a second embodiment of the present invention.
Figure 5:
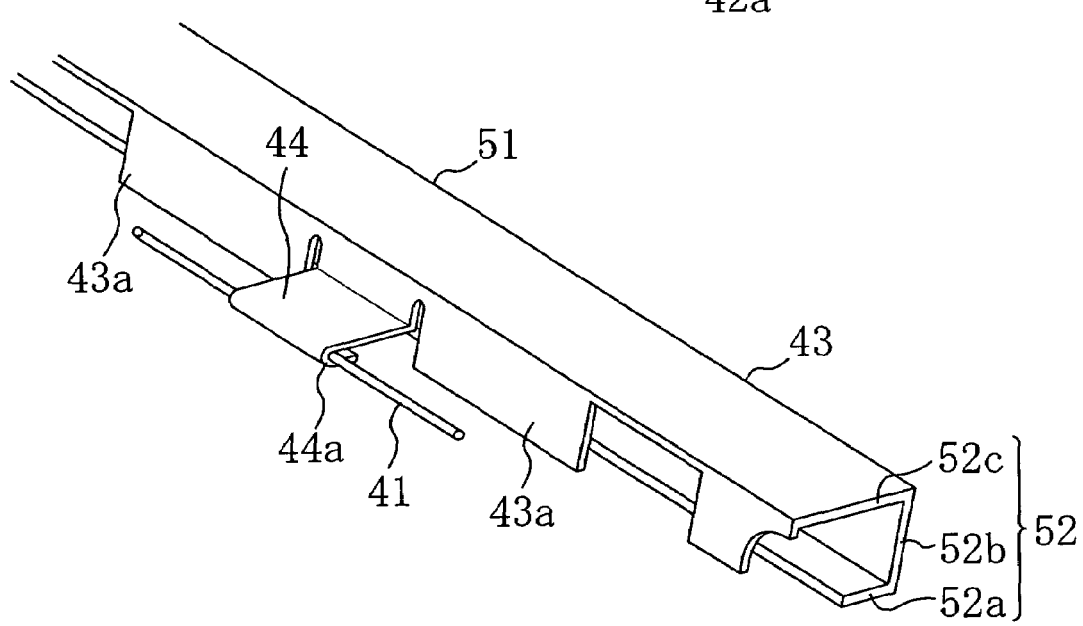
FIG. 5 is a perspective view which illustrates a resin-forming member of the discharge device of FIG. 4.

With reference to FIGS. 4 and 5, the present invention provides a second embodiment which is a variational example with a modification in the configuration of the discharge device (40) of the first embodiment. Accordingly, in the second embodiment, only the configuration of the discharge device (40) is described.

In the discharge device (40) of the second embodiment, the electrode holding member (43) and the fixing member (44) are integrally formed with each other by a sheet metal member (51) which is a plate of stainless steel. The sheet metal member (51) includes a main part (52) which is made up of a first flange (52*a*), a web (52*b*), and a second flange (52*c*), an electrode-faced surface (43*a*) which is a bend from the second flange (52*c*), and an electrode fixing plate (fixing member) (44) which is a bend from the second flange (52*c*). The electrode fixing plate (44) is provided, at its tip, with a folded part (44*a*). The folded part (44*a*) is caulked to hold the wire or rod-shaped discharge electrode (41).

The sheet metal member (51) is a stainless steel plate having a thickness of the order of from about 0.1 mm to about 0.2 mm. The discharge electrode (41) is a tungsten wire having a diameter dimension of 0.14 mm.

It should, however, be noted that the discharge electrode (41) is not necessarily a separate member to be firmly fixed to the electrode fixing plate (44). In other words, for example, the main part (52) of the sheet metal member (51), the electrode-faced surface (43*a*), the electrode fixing plate (44), and the discharge electrode (41) may be formed integrally by means of sheet metal processing.

The electrode-faced surface (43*a*) is formed on each side of the electrode fixing plate (44). And, with reference to FIG. 5, a single electrode fixing plate (44) and two electrode-faced surfaces (43*a*) form a single combination, in other words a plurality of such combinations (not shown), each comprising a single electrode fixing plate (44) and two electrode-faced surfaces (43*a*), are formed at predetermined intervals in the sheet metal member (51).

Also in this configuration, the wire or rod-shaped discharge electrode (41) is disposed parallel to the front portion (42*a*) of the counter electrode (42) and, in addition, the electrode-faced surface (43*a*) is disposed parallel to the discharge electrode (41) and to the front portion (42*a*). Accordingly, even when the tip portion of the discharge electrode (41) becomes worn out with the discharge, the distance between the discharge electrode (41) and the counter electrode (42) remains unchanged and is held constant and, in addition, the shape of the tip of the discharge electrode (41) remains substantially unchanged, thereby making it possible to generate stable streamer discharges.

Furthermore, the streamer discharge is stabilized by the arrangement that the discharge electrode (41) is disposed nearer to the electrode-faced surface (43*a*) relative to the counter electrode (42) and the arrangement that the discharge electrode (41) is held by the electrode fixing plate (44) so that the positional relationship between the discharge electrode (41) and the electrode-faced surface (43*a*) remains unchanged, which is the same as the first embodiment.

Still furthermore, the second embodiment also makes it possible to generate stable streamer discharges by satisfying the relational expressions (1)-(3) described in the first embodiment.

Variational Examples of the Second Embodiment

Figure 6:
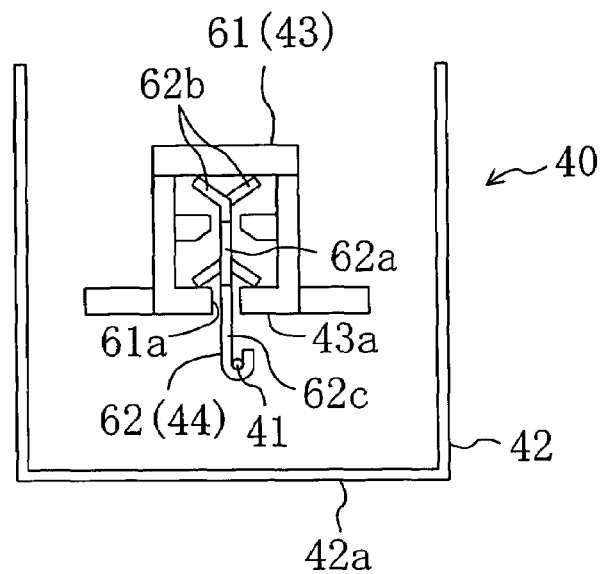
FIG. 6 is a constructional diagram of a discharge device according to a first variational example of the second embodiment.

With reference to FIG. 6, there is shown a first variational example of the second embodiment. In the first variational example, a long resin-forming member (61) is used as the electrode holding member (43). The resin-forming member (61) is shaped like a rectangular cylinder, and a slit (61*a*) is formed in the electrode-faced surface (43*a*). The fixing member (44) is formed by a sheet metal member (62) which is a plate of stainless steel. The sheet metal member (62) includes a main part (62*a*) extending through the inside of the resin-forming member (61) in longitudinal direction, a holding piece (62*b*) cut and turned up from the man part (62*a*) and in pressure contact with the 20 inner surface of the resin-forming member (61), and a fixing piece (62*c*) extending from the main part (62*a*) and holding the discharge electrode (41).

In the above configuration, the electrode holding member (43) is the resin-forming member (61). However, as mentioned above, even when the electrode holding member (43) is an insulator, it provides a function of stabilizing streamer discharges. Accordingly, the first variational example provides the same effects as the first and second embodiments.

Figure 7:
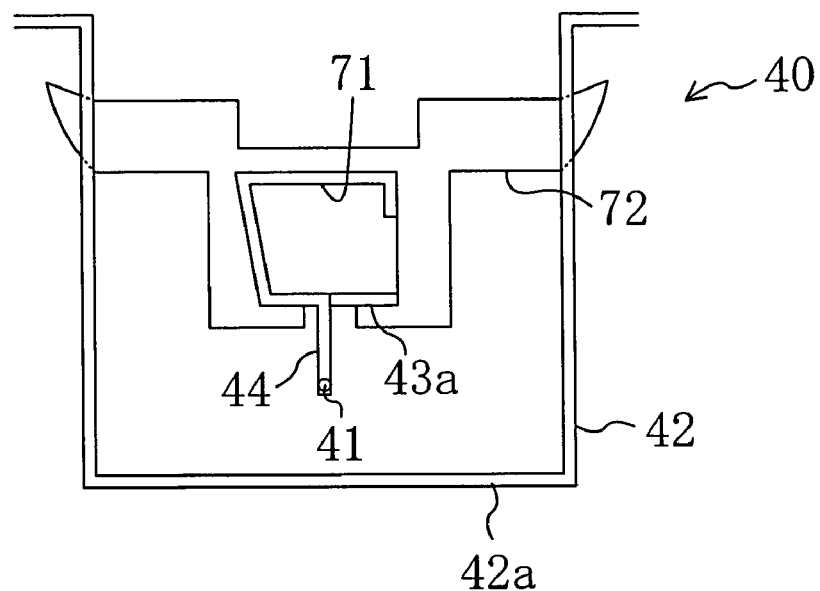
FIG. 7 is a constructional diagram of a discharge device according to a second variational example of the second embodiment.

With reference to FIG. 7, there is shown a second variational example of the second embodiment. In the second variational example, as an electrode holding member, a sheet metal member (71) is employed which has substantially the same shape as the 30 electrode holding member (43) shown in FIGS. 4 and 5. The sheet metal member (71) is not provided, at the tip of the electrode fixing plate (44), with the folded part (44a).

Instead, the discharge electrode (41) is firmly fixed to the electrode fixing plate (44) by welding. Other portions are constructed in the same way that their counterparts shown in FIGS. 4 and 5 are constructed. Like the example of FIGS. 4 and 5, as the stainless steel plate, one having, for example, a thickness of from 0.1 mm to 0.2 mm is used. As the discharge electrode (41), a tungsten wire having a diameter of about 0.14 mm is used.

The sheet metal member (71) is firmly fixed to the counter electrode (42) with a fixing insulator (72). Although not shown diagrammatically, the fixing insulator (72) is provided at each longitudinal end of the counter electrode (42). The arrangement that the sheet metal member (71) is firmly fixed to the counter electrode (42) by the use of the fixing insulator (72) is the same as the example of FIGS. 4 and 5.

Figure 8:
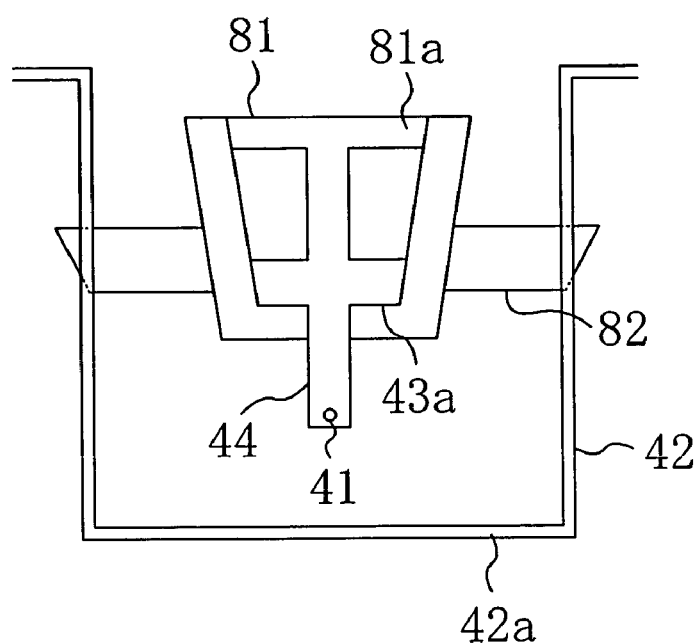
FIG. 8 is a constructional diagram of a discharge device according to a third variational example of the second embodiment.

With reference to FIG. 8, there is shown a third variational example of the second embodiment. In the third variational example, a forming member (81) of a conductive resin is used as an electrode holding member. The forming member (81) includes a substantially H-shaped main part (81a) and an electrode fixing plate (44) which extends outwardly from the main part (81a), wherein the discharge electrode (41) formed of a tungsten wire is firmly joined to the electrode fixing plate (44) by ultrasonic welding. In addition, as in the example of FIG. 7, the forming member (81) is firmly fixed to the counter electrode (42) by the use of the fixing insulator (82).

Also in the third variational example, the same effects as the first and second embodiments are obtained.

Third Embodiment of the Present Invention

Next, a third embodiment of the present invention is described in detail with reference to the drawings.

Figure 11:
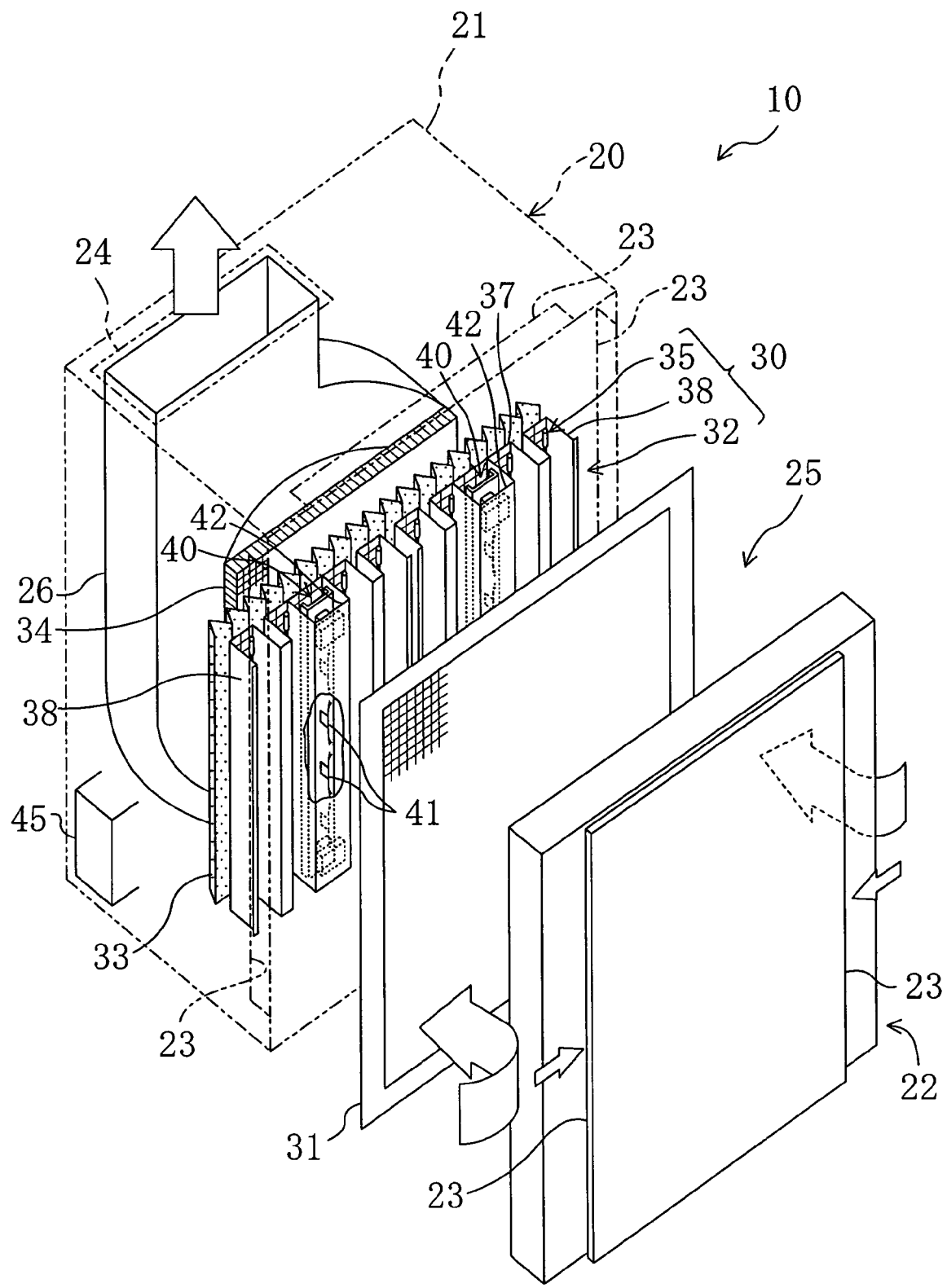
FIG. 11 is an exploded perspective view of an air purifying device according to a third embodiment of the present invention.
Figure 12:
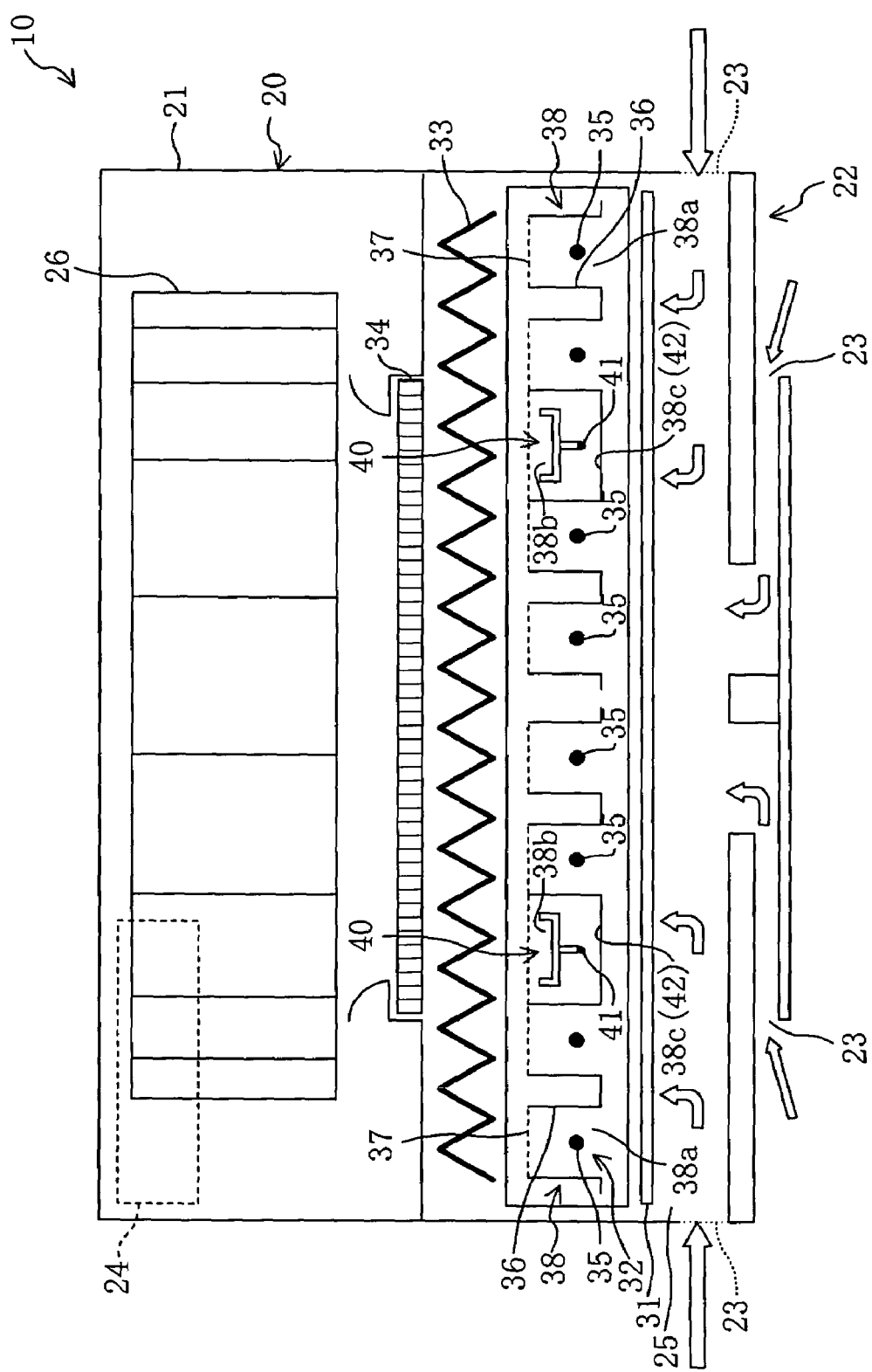
FIG. 12 is a view of the inside of the air purifying device of the third embodiment when viewed from above.

FIG. 11 is an exploded perspective view of the air purifying device (10) according to the third embodiment. FIG. 12 is a view of the inside of the air purifying device (10) when viewed from above. Like the air purifying device (10) of the first embodiment, the air purifying device (10) of the third embodiment is a household air purifying device for general household/smaller store use.

The air purifying device (10) includes a casing (20) made up of a box-like casing main body (21) one end of which is opened and a front plate (22) which is mounted to the open end of the casing main body (21). Air suction openings (23), through which room air as a gas to be treated is drawn in, are formed in both side surfaces of the casing main body (21), in a top surface of the casing main body (21), and in the center of the front surface of the front plate (22). In addition, formed in a portion of the top plate of the casing main body (21) adjacent to the back plate is an air blowout opening (24) through which room air flows outwardly.

Formed within the casing main body (21) is an air passageway (25) through which room air flows from the air suction opening (23) to the air blowout opening (24). Arranged, in sequence from the upstream side of the flow of air (the lower side in FIG. 12), along the air passageway (25) are a functional section (30) including various components for air cleaning, and a centrifugal air blower (26) for distribution of room air through the air passageway (25).

The functional section (30) is formed by such an arrangement that a pre-filter (31), an ionization part (32), a discharge device (40), an electrostatic filter (33), and a catalytic filter (34) are disposed in sequence from the side of the front plate (22). In addition, a power source means (45) of the discharge device (40) is disposed adjacent to the rear lower side of the casing main body (21) of the air purifying device (10).

The pre-filter (31) is disposed to entrap and collect dust of relatively large size present in the room air. The ionization part (32) causes dust of relatively small size passing through the pre-filter (31) to be electrically charged. The electrically charged dust is entrapped and collected by the electrostatic filter (33) (dust collecting filter) positioned downstream of the ionization part (32). The ionization part (32) is made up of a plurality of ionization lines (35) and counter electrodes (36) respectively associated with the ionization lines (35).

The plurality of ionization lines (35) are disposed on the front side of a corrugated member (38) having a corrugated horizontal cross section or a horizontal cross section shaped like a series of Japanese katakana characters "コ". In the present embodiment, two corrugated members (38) are disposed on the right side and on the left side, respectively. In addition, formed on the front side of the corrugated member (38) are a plurality of front-side openings (38a), and each ionization line (35) vertically extends across the corrugated member (38) from the top end to the bottom end within each front-side opening (38a). On the other hand, the counter electrode (36) associated with the ionization line (35) is provided on a wall surface forming the front-side opening (38a) of the corrugated member (38). A mesh plate (37) which is disposed parallel to the electrostatic filter (33) is coupled to a surface adjacent to the rear side of the corrugated member (38).

The discharge device (40) includes a plurality of discharge electrodes (41) and counter electrodes (42) each opposite to its associated discharge electrode (41).

Figure 13:
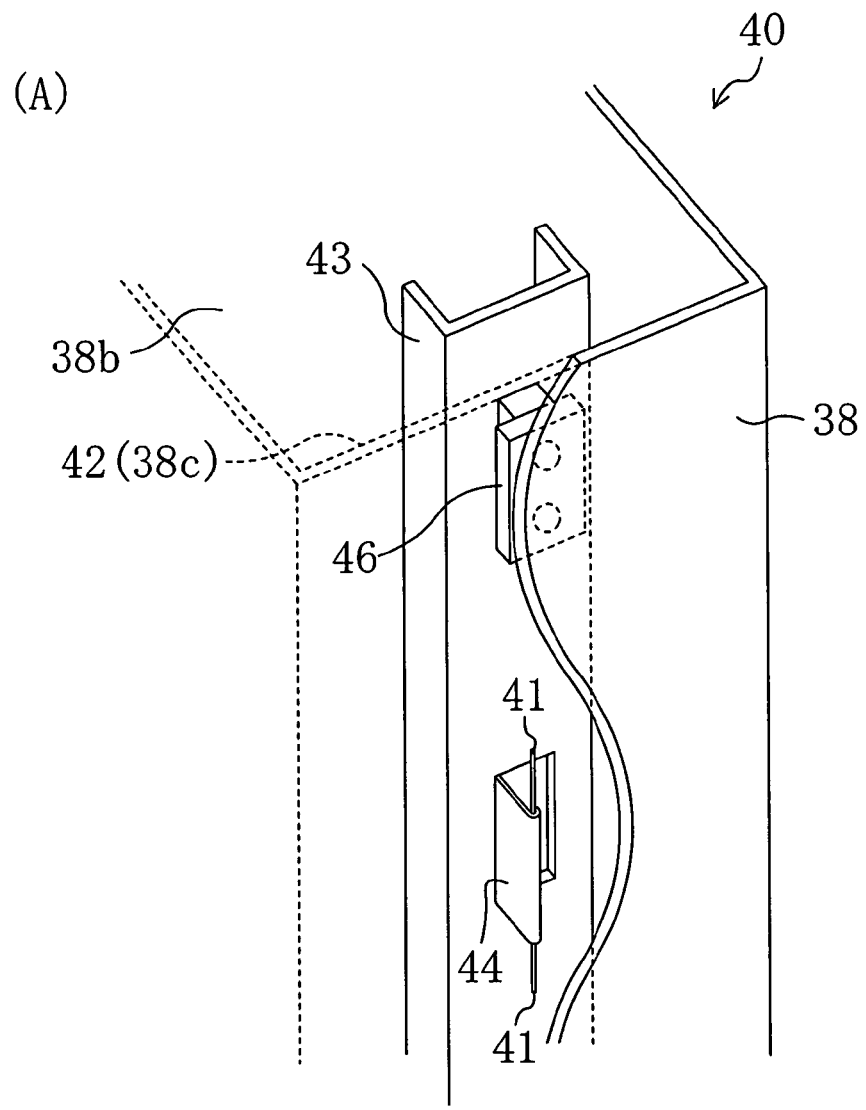
Figure 13:
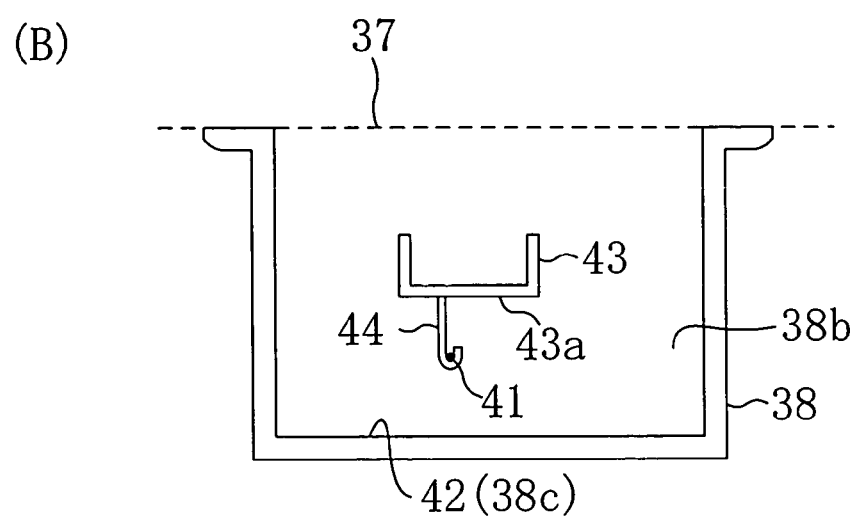

The discharge electrode (41) is shaped like a wire or rod. The discharge electrode (41) is disposed on the rear side of the corrugated member (38). As shown in FIG. 13(A) which is an enlarged perspective view of the discharge device (40), the discharge electrode (41) is disposed within a rear-side opening (38b) of the corrugated member (38) and is supported by the vertically-extending electrode holding member (43).

The electrode holding member (43) is formed, such that it has a horizontal cross section shaped like a Japanese katakana character "コ" and a plurality of supporting plates (fixing members) (44) which are formed so as to bent forwardly are formed at specific areas. And, the wire- or rod-shaped discharge electrode (41) is supported by a tip part of the supporting plate (44), the tip part being caulked so as to clamp the discharge electrode (41) (see FIG. 13(B) which is a horizontal cross sectional view of the discharge device). In the way as described above, both ends of the discharge electrode (41) are shaped, such that they vertically project from the supporting plate (44). In the present embodiment, tungsten is used as a material to form the discharge electrode (41).

On the other hand, the counter electrode (42) is formed at a first surface (rear surface) (38c) within the rear-side opening (38b) of the corrugated member (38) in which the discharge electrode (41) is disposed in the way as described above. And, the first surface (38c) functions as an electrode surface which faces towards the discharge electrode (41). In this way, the discharge electrode (41) projecting from the supporting plate (44) is disposed substantially parallel to the electrode surface of the counter electrode (42). Disposed at the upper and lower ends of the counter electrode (42) is a spacer (46) interposed between the counter electrode (42) and the electrode holding member (43). In the present embodiment, the spacer (46) is formed by an insulator. And, the distance (B) from the tip of the discharge electrode (41) to the counter electrode (42) is held constant by the spacer (46).

Here, the concrete configuration of each part of the discharge device (40) is described (see FIG. 3). In the first place, a relational expression (1) represented as: $0.96 \leq B/A \leq 1.52$ (more specifically, $1.16 \leq B/A \leq 1.45$) is satisfied where A is the spacing dimension between the discharge electrode (41) and the electrode-faced surface (43a) and B is the spacing dimension between the discharge electrode (41) and the counter electrode (42). The concrete numerical value of the spacing dimension, A, is: $4.4 \leq A$ (mm) $\leq 5.0$ ($4.7 \pm 0.3$) while on the other hand the concrete numerical value of the spacing dimension, B, is: $5.8 \leq B$ (mm) $\leq 6.4$ ($6.1 \pm 0.3$). In addition, a relational expression (2) represented as: $A \leq D$ (D=13 mm) is satisfied where A is the spacing dimension between the discharge electrode (41) and the electrode-faced surface (43a) and D is the width dimension of the electrode holding member (43) in the direction perpendicular to the axis of the discharge electrode (41). Furthermore, a relational expression (3) represented as: $B/E \geq 20$ is satisfied where E is the width dimension of the discharge electrode (41) relative to the surface direction of the counter electrode (42) or the diameter dimension of the discharge electrode (41) and B is the spacing dimension between the discharge electrode (41) and the counter electrode (42). The discharge electrode (41) is formed of a tungsten wire whose diameter dimension, E, is Φ0.2 mm and whose length dimension, C, i.e., the projection dimension of the discharge electrode (41) from the fixing member (44), is (3.5+0.5) mm.

The electrostatic filter (33) is disposed downstream of the discharge device (40). The electrostatic filter (33) entraps and collects, at its upstream side surface, dust of relatively small size electrically charged by the above-described ionization part (32). The electrostatic filter (33) supports, on its downstream side surface, a photocatalyst (photosemiconductor). The photocatalyst further activates high-reactivity substances (activated species such as electron, ion, ozone, and radical) present in a low-temperature plasma generated by the discharge of the discharge device (40), thereby promoting the decomposition of harmful substances and odorous substances present in the room air. As the photocatalyst, titanium dioxide and zinc oxide, or oxides of tungsten and cadmium sulfide may be used. In addition, the electrostatic filter (33) is formed by a so-called pleated filter having a corrugatingly-bent horizontal cross section.

The catalytic filter (34) is disposed downstream of the electrostatic filter (33). The catalytic filter (34) is formed by a honeycomb-structure substrate which supports on its surface a plasma catalyst. This plasma catalyst, like the aforesaid photocatalyst, further activates high-reactivity substances (activated species such as electron, ion, ozone, and radical) present in a low-temperature plasma generated by the discharge of the discharge device (40), and promotes the decomposition of harmful substances and odorous substances which are components to be treated in the room air. As the plasma catalyst, a catalyst of the manganese family, a catalyst of the precious metal family, or a catalyst formed by addition of an adsorbent, e.g., activated carbon, to such a catalyst may be used.

Running Operation

When the air purifying device (10) is in operation, the centrifugal air blower (26) starts operating, and room air which is a gas to be treated flows and passes through the air passageway (25) within the casing main body (21). In addition, in this state, high voltages are applied, by the power source means (45), to the ionization part (32) and to the discharge device (40).

Upon introduction of the room air into the casing main body (21), dust of relatively large size is first removed by the pre-filter (31). After the passage through the pre-filter (31), the room air flows to the ionization part (32). In the ionization part (32), dust of relatively small size present in the room air is electrically charged by discharge between the ionization line (35) and the counter electrode (36). The room air containing the electrically charged dust flows into the electrostatic filter (33). The electrostatic filter (33) entraps and collects the electrically charged dust particles.

On the other hand, in the discharge device (40), there is generated a low-temperature plasma by streamer discharge between the discharge electrode (41) and the counter electrode (42). The low-temperature plasma generated by the discharge device (40) flows downstream together with the room air.

The low-temperature plasma contains therein a high-reactivity substance (activated species). And, when coming into contact with the room air, the high-reactivity substance decomposes harmful substances and odorous substances present in the room air.

In addition, when the activated species reaches the electrostatic filter (33), it is activated to a further extent by the photocatalyst supported on the electrostatic filter (33), as a result of which the harmful and odorous substances in the room air are decomposed to a further extent. And, when the activated species reaches the catalytic filter (34), these substances are further activated, as a result of which the harmful and odorous substances in the room air are decomposed to a still father extent.

The room air, purified by removal of dust, harmful substances, and odorous substances, is taken into the centrifugal air blower (26) and is blown out into the room through the air blowout opening (24).

Next, the operation by the concrete configuration of each part is described (see FIG. 3).

As described above, the discharge device satisfies the foregoing three relational expressions: the relational expression (1) represented as: $0.96 \leq B/A \leq 1.52$ (more specifically, $1.16 \leq B/A \leq 1.45$) where A is the spacing dimension between the discharge electrode (41) and the electrode-faced surface (43a) and B is the spacing dimension between the discharge electrode (41) and the counter electrode (42); the relational expression (2) represented as: $A \leq D$ where A is the spacing dimension between the discharge electrode (41) and the electrode-faced surface (43a) and D is the width dimension of the electrode holding member (43) in the direction perpendicular to the axis of the discharge electrode (41); and the relational expression (3) represented as $B/E \geq 20$ where E is the width dimension of the discharge electrode (41) relative to the surface direction of the counter electrode (42) or the diameter dimension of the discharge electrode (41) and B is the spacing dimension between the discharge electrode (41) and the counter electrode (42).

With regard to the relational expression (1), as already described by making use of FIGS. 9 and 14, if the value of B/A falls below 0.96, this becomes prone to causing a glow discharge to be generated. On the other hand, if the value of B/A exceeds 1.52, this intensifies the tendency towards spark generation. As a result, the maintenance of generating stable discharges becomes difficult. Further, simultaneous generation of discharges at a plurality of points becomes difficult. On the other hand, if $0.96 \leq B/A \leq 1.52$ (especially, $1.16 \leq B/A \leq 1.45$), this becomes less prone to causing a glow discharge or spark to be generated. As a result, it becomes possible to generate a stable streamer discharge.

With regard to the relational expression (2), if the spacing dimension, A, exceeds the width dimension, D, this weakens the action of the electrode-faced surface relieving the electric field convergence on the tip of the discharge electrode (41). On the other hand, if it is arranged such that the relational expression (2) represented as: $A \leq D$ is satisfied, this assures that the action of relieving the electric field convergence on the tip of the discharge electrode (41) is obtained, thereby making it possible to generate a stable streamer discharge.

Additionally, with regard to the relational expression (3), if the value of B/E is less than 20, this increases the width or the diameter of the discharge electrode (41) relative to the distance between the discharge electrode (41) and the counter electrode (42). As a result, the discharge characteristic tends to change due to the wear of the tip of the discharge electrode (41) and its variation, and the streamer discharge becomes unstable and discharges in a plurality of discharge electrodes (41) become uneven. On the other hand, if $B/E \geq 20$, this makes the width or the diameter of the discharge electrode (41) small enough relative to the distance between the discharge electrode (41) and the counter electrode (42), thereby reducing the effect that the wear of the tip of the discharge electrode (41) and its variation have on the discharge. As a result, it becomes possible to generate stable streamer discharges. In addition, if it is arranged such that $B/E \geq 30$, this turns down the sound of streamer discharges, as proved by the experimental results.

Effects of the Third Embodiment

As described above, also in the third embodiment, the discharge electrode (41) in the shape of a wire or rod is disposed substantially parallel to the counter electrode (42) in the shape of a sheet so that, even when the tip of the discharge electrode (41) becomes worn out, the distance between the discharge electrode (41) and the counter electrode (42) is held constant and the shape of the tip of the discharge electrode (41) remains unchanged. Therefore, it becomes possible to maintain the discharge characteristic, and the streamer discharge is stabilized. Accordingly, problems, such as the generation of a spark due to the change in shape of the discharge electrode (41) with time and the generation of a glow discharge instead of the generation of a streamer discharge, can be avoided.

In addition, because of the arrangement that the electrode holding member (43) is disposed so as to face the counter electrode (42) with the discharge electrode (41) interposed therebetween, it becomes possible to relieve the electric field convergence on the tip of the discharge electrode (41), thereby making it possible to stabilize the streamer discharge.

Furthermore, it becomes possible to generate stable streamer discharges by the following arrangements: the electrode-faced surface (43a) is disposed substantially parallel to the discharge electrode (41) and to the counter electrode (42) so that, even when the tip of the discharge electrode (41) becomes gradually worn out, neither the distance between the discharge electrode (41) and the counter electrode (42) nor the distance between the discharge electrode (41) and the electrode-faced surface (43a) changes; the discharge electrode (41) is disposed nearer to the electrode-faced surface (43a) relative to the counter electrode (42) so that a glow discharge is less prone to being generated; the fixing member (44) for firmly fixing the discharge electrode (41) to the electrode holding member (43) is provided so that the positional relationship between the discharge electrode (41), and the counter electrode (42) and the electrode holding member (43) is made stable; and the foregoing relational expressions (1)-(3) are satisfied.

In addition, in the present embodiment, the power source means (45) is formed by a direct-current power source, thereby making it possible to manufacture the discharge device (40) at lower costs in comparison with the case where pulse power sources are employed.

Furthermore, the discharge electrode (41) is formed of a material of tungsten. Since the tungsten material has a high degree of hardness, the discharge electrode (41) undergoes less warpage or deformation, thereby facilitating the manufacture thereof. In addition, since the tungsten material has a high melting point and a high degree of heat conductivity, this reduces the wear of the discharge electrode (41) due to the discharge, thereby enhancing the durability thereof. In addition, the tungsten material has characteristics that, when the tip of the discharge electrode (41) becomes worn out by small degrees with the discharge, the tip becomes rough, thereby accomplishing improvement in streamer discharge stability.

Other Embodiments

With respect to the foregoing embodiments, the present invention may be configured as follows.

For example, the first embodiment may be arranged such that a plurality of air vents are formed in the front portion (42a) of the counter electrode (42). As a result of such arrangement, when room air introduced into the casing (10) flows downstream, the room air flows also through a streamer discharge place within the counter electrode (42). As a result, activated species et cetera in a low-temperature plasma generated by streamer discharge are not retained within the counter electrode (42). That is, the activated species flow to the catalytic filter (34) without fail. Accordingly, the processing capacity of the air purifying device can be stabilized at high level.

In addition, each of the foregoing embodiments has been described in terms of an example where the discharge device of the present invention is applied to an air purifying device. The scope of application of the discharge device of the present invention is not limited to air purifying devices. The discharge device of the present invention is applicable to other machinery and equipment for generating streamer discharges. However, when the discharge device of the present invention is applied to air purifying devices, it becomes possible to make use of the streamer discharge characteristic with remarkable efficiency.

In addition, in the foregoing embodiments, the catalytic filter (34) which comprises a substrate which supports thereon a plasma catalyst such as a catalyst of the manganese family and a catalyst of the precious metal family, is disposed downstream of the discharge device (40). Alternatively, it may be arranged such that, in place of the catalytic filter (34), an adsorptive treatment member comprising a substrate which supports thereon an adsorbent such as activated carbon and zeolite is disposed downstream of the discharge device (40).

INDUSTRIAL APPLICABILITY

As has been described above, the present invention is useful with discharge devices for generating a streamer discharge between the tip of a discharge electrode and a counter electrode, and with air purifying devices employing such a discharge device.

What is claimed is:

1. A discharge device comprising:
   a discharge electrode;
   a counter electrode facing towards the discharge electrode; and
   a power source for applying discharge voltages to the discharge and counter electrodes, the power source being configured to generate a streamer discharge from a tip of the discharge electrode towards the counter electrode,
   the discharge electrode being in a shape of a wire or rod and being disposed substantially parallel to the counter electrode; and
   an electrode-faced member disposed so as to face the counter electrode across the discharge electrode, the electrode-faced member having an electrode-faced surface opposite to the counter electrode.

2. The discharge device of claim 1 wherein the counter electrode is in a shape of a sheet.

3. The discharge device of claim 1 wherein the electrode-faced surface is substantially parallel to both the discharge electrode and the counter electrode.

4. The discharge device of claim 3 wherein the discharge electrode is disposed either at a position intermediately between the counter electrode and the electrode-faced surface or at a position nearer to the electrode-faced surface relative to the intermediate position.

5. The discharge device of claim 1 wherein the electrode-faced member and the discharge electrode are formed of different materials.

6. The discharge device of claim 5 wherein the electrode-faced member is formed of an insulating material.

7. The discharge device of claim 1 further comprising a fixing member for firmly fixing the discharge electrode to the electrode-faced member, the tip of the discharge electrode projecting from the fixing member.

8. The discharge device of claim 1 wherein a relational expression represented as: $0.96 \leq B/A \leq 1.52$ is satisfied where A is a spacing dimension between the discharge electrode and the electrode-faced surface and B is a spacing dimension between the discharge electrode and the counter electrode.

9. The discharge device of claim 1 wherein the electrode-faced member has a predetermined width dimension, D, in a direction perpendicular to an axis of the discharge electrode, and a second relational expression represented as: $A \leq D$ is satisfied where A is a spacing dimension between the discharge electrode and the electrode-faced surface.

10. The discharge device of claim 1 wherein a relational expression represented as: $B/B \geq 20$ is satisfied where B is a width dimension of the discharge electrode relative to a surface direction of the counter electrode or a diameter dimension of the discharge electrode and B is a spacing dimension between the discharge electrode and the counter electrode.

11. The discharge device of claim 1 wherein the power source includes a direct-current power source.

12. The discharge device of claim 1 wherein the discharge electrode is formed of a tungsten material.

13. An air purifying device comprising:
   an air passageway through which air to be treated flows; and
   a discharge device disposed in the air passageway for generating a streamer discharge, the discharge device being formed by the discharge device as set forth in claim 1.

* * * * *